(12) United States Patent
Cox

(10) Patent No.: US 8,020,815 B2
(45) Date of Patent: Sep. 20, 2011

(54) MODULAR STAND WITH MOUNTING PROVISIONS

(75) Inventor: James Mark Cox, Winchester, CA (US)

(73) Assignee: Pryor Products, Oceanside, CA (US)

( * ) Notice: Subject to any disclaimer, the term of this patent is extended or adjusted under 35 U.S.C. 154(b) by 0 days.

(21) Appl. No.: 12/688,759

(22) Filed: Jan. 15, 2010

(65) Prior Publication Data

US 2011/0174936 A1    Jul. 21, 2011

(51) Int. Cl.
*F16L 3/00* (2006.01)
(52) U.S. Cl. ........................................ 248/121; 248/129
(58) Field of Classification Search .................. 248/129, 248/121, 146, 158, 127
See application file for complete search history.

(56) References Cited

U.S. PATENT DOCUMENTS

| | | | |
|---|---|---|---|
| 2,627,904 A | 2/1953 | Thieman | |
| 4,474,202 A | 10/1984 | Blechner | |
| 4,905,944 A * | 3/1990 | Jost et al. | 248/125.8 |
| 4,907,794 A | 3/1990 | Rose | |
| 5,152,730 A | 10/1992 | Hoffman | |
| 5,520,597 A | 5/1996 | Tobin | |
| 5,538,268 A | 7/1996 | Miller | |
| 5,800,318 A | 9/1998 | Coviello | |
| 5,803,103 A | 9/1998 | Haruyama | |
| 6,361,001 B1 * | 3/2002 | Durand | 248/146 |
| 6,733,018 B2 | 5/2004 | Razon | |
| 6,912,960 B2 | 7/2005 | Tsai | |
| 7,093,809 B2 * | 8/2006 | Hwang | 248/166 |
| 7,628,360 B2 * | 12/2009 | Anthes et al. | 248/125.8 |
| 7,806,376 B2 * | 10/2010 | Song et al. | 248/177.1 |
| 2006/0196997 A1 * | 9/2006 | Johnson | 248/129 |
| 2007/0023073 A1 | 2/2007 | Su | |
| 2009/0184217 A1 * | 7/2009 | Sprout | 248/124.1 |
| 2010/0212708 A1 * | 8/2010 | Turner et al. | 135/67 |

OTHER PUBLICATIONS

INTERMED; Anesthesia and Mechanical Ventilation; Brochure; Published as early as Nov. 2008; 8 pages; Intermed; Brazil (Distributed at a trade show in Germany 2008).

* cited by examiner

*Primary Examiner* — Ramon O Ramirez
(74) *Attorney, Agent, or Firm* — Gordon & Rees LLP

(57) ABSTRACT

The stand has modules to form a support base with elongated support members with wheels or legs. The stand can either incorporate two spaced load supporting posts or a single post extending from a spanner module that connects between the elongated support members. When two load support members are employed the user can step between the posts. When a single post and spanner are employed the user can step as far as the spanner near the center of support. The support members diverge from their centers provide a wide stance of the wheels or legs for stability. At the upper end of the post or posts a load support platform is carried either directly on a single post or through a cross-piece on a two post configuration. T-shaped slots in the post can be utilized to attach loads to the posts and a panel extending between posts. In either configuration a spilt wheel at the level of the load support allows for the user to maneuver a wheeled version of the stand and serves as a fender protecting equipment carried on the load support platform.

29 Claims, 7 Drawing Sheets

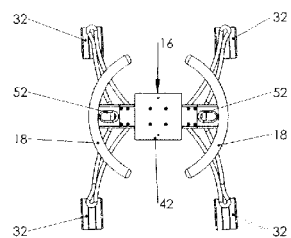
FIG. 4
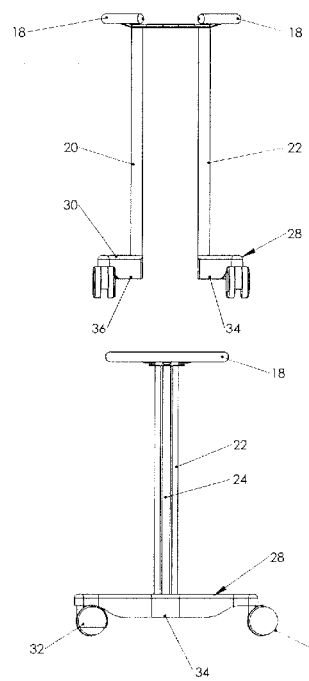
FIG. 2
FIG. 3
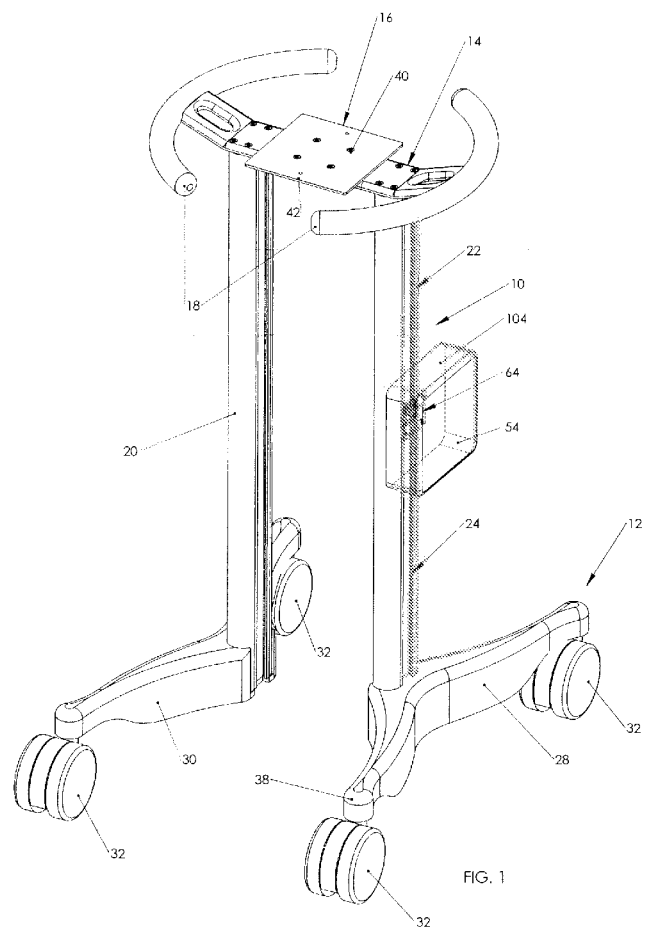
FIG. 1

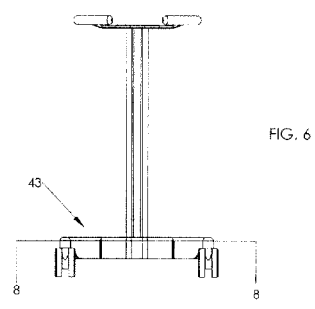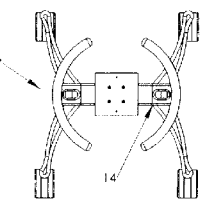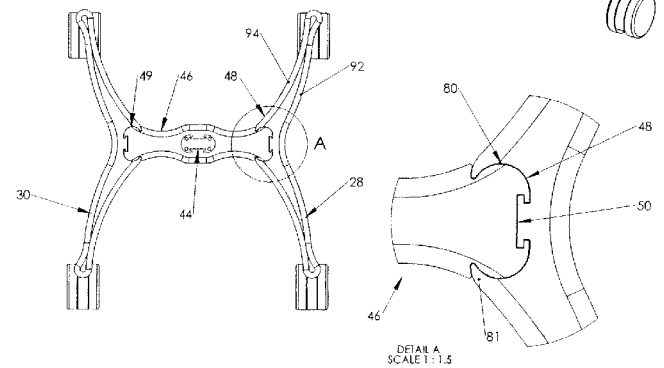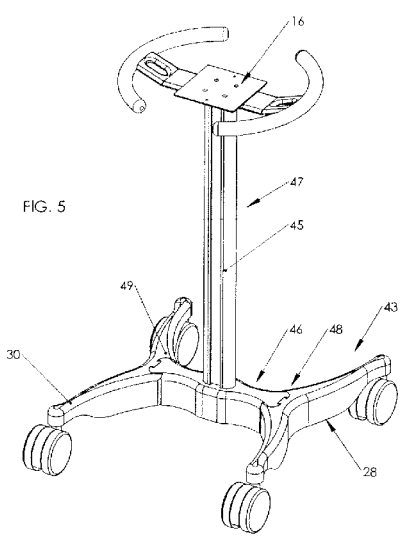
FIG. 6
FIG. 6A
FIG. 5
FIG. 7
FIG. 8
FIG. 9
DETAIL A
SCALE 1:1.5

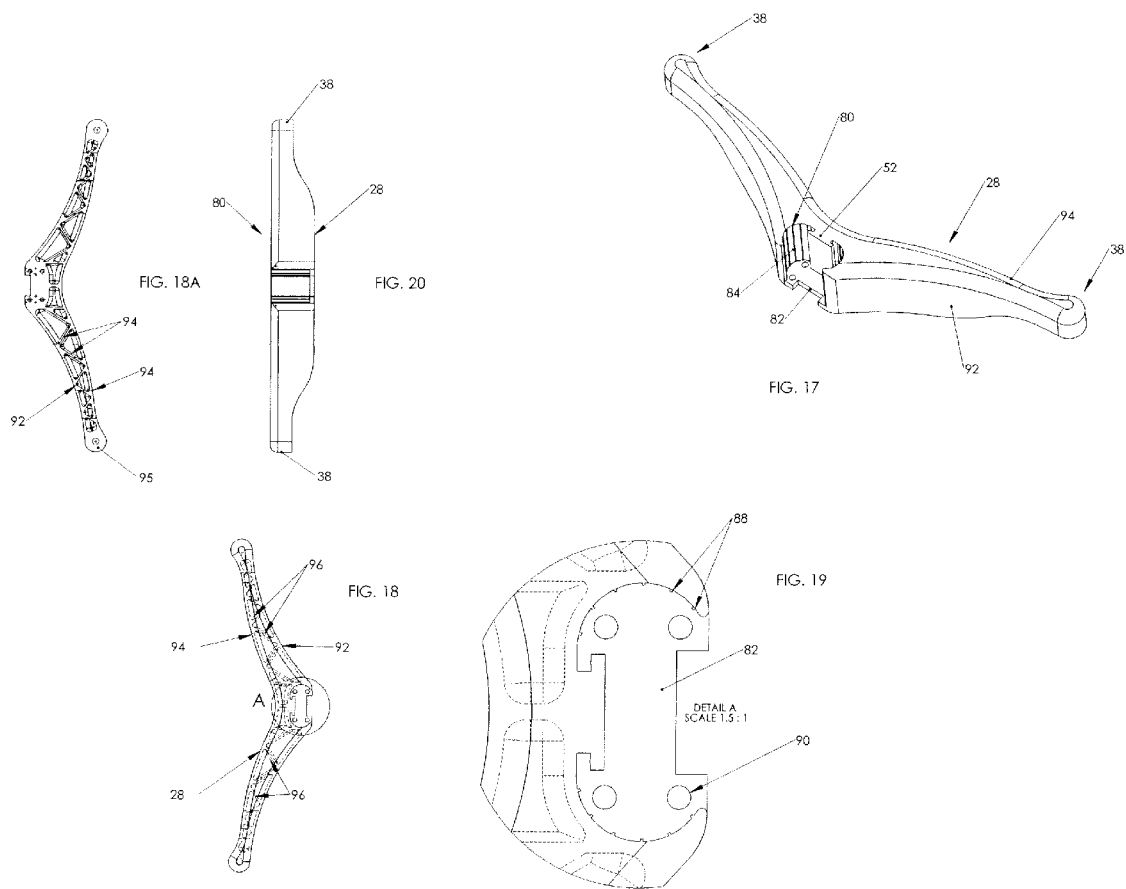

MODULAR STAND WITH MOUNTING PROVISIONS

FIELD OF THE INVENTION

The present invention relates generally to stands that support a load above a base, and more particularly to stands to support medical devices and accessories on a wheeled base.

BACKGROUND OF THE INVENTION

Medical Stands have evolved from IV stands which were originally designed to support containers of IV fluids into general purpose equipment stands. The original designs typically had a first central pole on a wheeled base rising to approximately 3 feet above the base and then a smaller diameter pole journaled in and rising from the first pole, to support an IV tree from which one or more IV containers could be hung. The wheeled base would support castering wheels at the end of three or more base legs that radiate from a central core. More recently these stands have been pressed into service to support medical equipment including IV pumps, ventilators and the like. Much of this medical equipment has grown in size as other functions are incorporated. The current designs of stands may be too spindly and top heavy to provide confidence that the medical equipment will be protected from damage from tip over and the patient protected from injury when using the stand as an ambulatory aid. As a stop-gap measure additional legs can be added to the three minimum legs. As a result stands may provide four or five or even six legs for greater stability. Handles have been added to make it easier for medical personnel to move the stands into position, and for ambulatory patients to push the stands in front of them when they walk while remaining connected to the attached medial equipment. However, the large number of legs represents a trip hazard for both the medical personnel and patients especially as the user approaches the stand to move it.

The various requirements of different devices and uses has lead to the design of custom stands that share few or no common parts and therefore are more expensive to manufacture.

SUMMARY OF THE INVENTION

As used herein "center of support" means the central location substantially equidistant from each of the engagement supports. In the exemplary embodiment there are four engagement supports on a support base which together define a rectangle. The center of support in this configuration is at the intersection of diagonals from opposing corners of the rectangle. In the exemplary embodiment the engagement supports are castering wheels that roll on a floor and are mounted at the ends of elongated support members. The floor engagement supports and elongated support members together comprise a support base. In an alternative configuration fixed legs can be employed instead of wheels to function as floor engagement supports when moving the stand is not required or desired. It will be appreciated that in either configuration the stand may be utilized on other horizontal surfaces besides a floor surface so that when the term "floor" is employed herein it is intended to include any suitable horizontal surface.

The elongated support members have a central post mount which in the exemplary embodiment is an opening which can be used to receive support posts that extend vertically from the elongated support members. In an alternative embodiment the post mounts can be protrusions from said elongated support members that are shaped to engage the interior openings in said support posts. When two support posts are employed they are joined at their upper ends by a cross-piece that structurally interconnects the two support posts. Both mounting structures lend themselves to the exemplary embodiment with vertical support posts but alternatively can mount the posts to be at an angle so that the posts are inclined and either cross before the cross piece or come together at the cross piece. As a still further alternative the posts may be inclined to overly the elongated members and the inclinations can be in the same direction for each support post or in opposite directions so a to create a Z appearance when viewed from the side. With vertical or inclined orientation of the posts, the length of the cross piece dictates the spacing between the elongated support members. Thus stands requiring various different widths can be accommodated merely by varying the length of the cross-piece. For clarity all further discussion of the support posts will be based on the use of posts with a vertical orientation and the use of openings for the posts in the elongated support members, rather than protrusions from the elongated support members.

The preferably extruded aluminum and therefore have a uniform cross-section. A feature of the invention is that the support posts have t-shaped slots on both sides. These slots facilitate the mounting on the stand of a wide variety of equipment such as pumps, batteries used to power the equipment on the load support platform and oxygen cylinders. The fact that the t-shaped grooves run the full length of the support post makes it possible to quickly attach the extra equipment at a location that does not interfere with existing mounted devices. To facilitate the mounting a dovetail bracket is provided with a flange that is sized to fit into the opening of the t-shaped slot when it is orientated with its narrow width aligned with the opening and then provides for rotating the flange with a knob or nut so that the flange engages the wall of the slot and opening and upon further tightening of the knob or nut, the flange frictionally engages the walls of the slot to support the equipment.

The cross-piece can mount, at its center, a load support platform. In this position the load support platform is located at the center of support and equipment mounted there will add little or no tipping torque. The support posts may incorporate one or more t-shaped slots along their length which can be used to connect medical equipment or provide for supporting an inter-connecting panel between the support posts.

When used, the inter-connecting panel is desirably of a planar configuration and when attached to the support posts adds additional rigidity to the structure. In the exemplary embodiment the panel is attached with t-shaped keys that slide into the t-shaped slots. Another important function of the inter-connecting panel is that is provides a support surface for medical equipment and accessories, while at the same time providing a display surface which can display textual material such as instructions or warnings on the use of the stand, and can display equipment manufacturers logos to associate the stand with a particular medical equipment manufacturer.

A feature of the invention is that two distinct configurations of the stand can be produced by optionally incorporating one unique part together with multiple use parts. The unique part is a spanner piece which terminates at its ends with engagement knobs having the same cross-section as the support posts, so that the spanner piece can be received in the central openings of the elongated support members to structurally interconnect the elongated support members into an H-shaped base. The spanner has a centrally located opening to receive a single central support post.

A cross-piece that spans between the upper ends of the posts in a two post configuration can also be used to mount part-circular handles in a single post configuration. This piece can be unique if it has different mounting openings for the support posts or can be in a multiple use configuration if a piece with the mounting openings for support posts are left unused in a single post configuration.

All of the other parts including elongated support members, posts and brackets can be used in either configuration.

In either configuration that support post or posts may desirably terminate in a load support platform carried by a cross-piece interconnecting the post or posts to push-pull handles of the split wheel type. The part-circular handles allow medical personnel to position the stand at the point of use and serve as a fender to prevent damage to the medical equipment carried on the load support platform. These handles can also be used to move the stand by a patient who remains attached to medical equipment while using the stand for ambulatory support. The load support platform may desirably be a flat plate to engage the undersurface of medical equipment and have fastener openings to secure the medical equipment in place.

BRIEF DESCRIPTION OF THE DRAWINGS

These and other features of the invention are described in further detail in the following description and will be better understood with reference to the accompanying drawings, which are briefly described below.

FIG. 1 shows an isometric view of the stand in a step through configuration.

FIG. 2 shows a front view of the stand of FIG. 1.

FIG. 3 shows a side elevation view of the stand of FIG. 1.

FIG. 4 shows a top view of the stand of FIG. 1.

FIG. 5 shows a isometric view of the stand in a H-base configuration.

FIG. 6 shows a front view of the stand of FIG. 5.

FIG. 6A shows a side view of the stand of FIG. 5.

FIG. 7 shows a top view of the stand of FIG. 5.

FIG. 8 shows a sectional view of the stand taken on line 8-8 of FIG. 6.

FIG. 9 shows a detail of the portion of the area A in FIG. 8, and shows how the knob on a spanner piece is received in the central opening of an elongated support member.

FIG. 17 is an isometric view of the elongated support member.

FIG. 18 is a top view of the elongated support member showing the stiffening webs in dotted lines and the floor of the post opening.

FIG. 18A a is a bottom view of the elongated support member showing the stiffening webs.

FIG. 19 is an enlarged view taken on the A section of FIG. 18 and showing the compression ribs in the post opening.

FIG. 20 is a side elevation view of the elongated support member showing the height of the sides of the elongated support member as they taper from the greatest height at the center to the least height at the ends.

DETAILED DESCRIPTION

Figure 12:
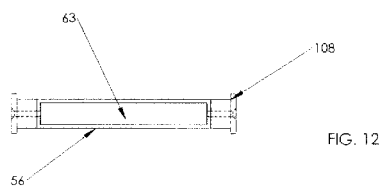
FIG. 12 is a sectional view taken on line 12-12 of FIG. 11. showing the shaft of the dovetail bracket which terminates in a knob or nut which can be used to firmly engage the dovetail bracket with the t-shaped slot.

Exemplary embodiments of the invention are described in detail below with reference to the appended figures, wherein like elements are referenced with like numerals throughout. The figures are not necessarily drawn to scale and do not necessarily show every detail or structure of the various embodiments of the invention, but rather illustrate exemplary embodiments and mechanical features in order to provide an enabling description of such embodiments.

FIG. 1 shows a wheeled stand 10 with a base 12 and a cross-piece 14 which mounts a support plate 16 and twin part-circular handles 18. The preferred material for the cross piece is aluminum with the handles being of aluminum with painted grips. The base 12 comprises two elongated support members 28 and 30 which mount four castering wheels 32 in end bosses of which boss 38 is representative. The support members 28 and 30 are identical and are merely reversed end for end to serve on either side of the stand. The fact that the support members are identical reduces manufacturing costs and parts inventory. The support members are preferably molded of ABS Polycarbonate blend or nylon. The elongated support members curve inwardly toward their centers and thus have a wide opening for the feet of users and widely space the castering wheels 32 for stability. Posts 20 and 22 are shown mounted in the elongated support members 30 and 28 respectively. The support posts 20 and 22 have each have two t-shaped slots of which slots 24 and 26 are visible. (See FIG. 21 for further details). The posts have a uniform cross-section and may desirably be of extruded aluminum. The posts have parallel sides (the sides that accommodate the t-shaped slots) and have rounded ends. Thus there are no sharp edges or protrusions to cause injury to users that inadvertently contact the posts with their feet or legs. The posts are identical and therefore, as with the elongated support members, which reduces tooling, manufacturing and parts inventory costs. A dovetail bracket 64 is shown as being mounted and secured in the t-shaped slot 24 and carries a representative piece of equipment 54 (shown in dotted lines). The details of the brackets are shown in FIGS. 13-16. Posts 20 and 22 terminate at their upper ends being attached to cross piece 14 which spaces and stiffens the post and base connection. Cross piece 14 extends beyond the posts to provide a mount for part-circular handle grips 18. The center of the cross-piece supports an equipment mount plate 16 secured through fastener openings of which opening 40 is representative. Equipment (not shown) can be secured to the plate through mounting openings of which opening 42 is representative. Since the mounted equipment will be centrally located and over the center of support, the equipment is protected from impact with walls and other obstacles by the hand grips 18 and is resistant to tipping because of the span of the elongated members 28 and 30.

FIG. 2 shows the stand in a frontal view which shows the undersides 34 and 36 of the of the elongated support members. The support members slope downwardly toward the center so that the center of gravity of the base is as low as possible while still providing for sufficient clearance to accommodate large castering wheels.

FIG. 3 shows a side view of the stand from the right side of FIG. 2. The elongated support member 28 shows the slope referenced in FIG. 2. The elongated support member 28 carries post 22.

FIG. 4 shows a top view of the step through configuration. Spaced castering wheels 32 are shown to be widely spaced side to side and fore and aft to provide a stable stance for the stand. The center of support is located directly under the support plate 16 so that equipment mounted through the mounting openings 42 will be balanced and not exert any tipping moment on the stand 10. This view also shows openings 52 in the cross-piece. These openings lighten the structure of the upper support portion of the stand to further minimize the potential for tipping. The openings 52 may also be used to guide cables and cords from the equipment mounted on the mounting plate to auxiliary equipment mounted on the posts and to guide power cords down the stand to be inserted into an electrical outlet for powering the equipment or charging on-board batteries.

FIGS. 5-9 show the stand in an H-base configuration. Referring to FIG. 5, it will appear that all of the components of the stand 47, are of identical configuration to those used in the step-through configuration except that a spanner piece 46 is used to connect the elongated members 28 and 30 at the base. The spanner piece 46 incorporates a central opening 44 (see FIG. 8) that has a generally oval shape corresponding to the openings in the elongated support members 28 and 30. The spanner terminates in end knobs 48 and 49 that are received in the openings in the elongated members 28 and 30. (See detail of a representative opening 80 in FIG. 17). While spanners of various lengths can be employed, the specific spanner illustrated produces the same wide stance of the elongated members as that produced in the step-through configuration of FIGS. 1-5. A single post 45 is received in the opening 44. This post may be identical to the posts 20 and 22 and therefore shares the cost benefit of a minimum parts count for the a stand that is available in two distinct configurations (step-through and H-base). The post 45 is carried on the base 43 at the center of support and therefore takes maximum advantage of the wide stance of the elongated members 28 and 30 to provide a very stable platform for an elevated load such as a load carried on the support plate 16. While the H-base of FIGS. 5-9 does not permit a user to step beyond the center of support, the open and outwardly curving stance of the elongated support members provides a deep space that may be referred to as a step-in space. A user grasping the two part-circular handles is positioned so that in an ordinary stride the users feet will not contact the spanner 46 or any other part of the stand.

Referring to FIG. 6 the location of the section line 8-8 is shown to pass through the various components of the base 43. Thus the sectional view of FIG. 8 shows the elongated members to be comprised of spaced sides of which sides 92 and 94 are representative. The central opening 44 has the same interior shape as the exterior shape of the post 45. A end plate 82 is integrally molded at the bottom of the opening 44 and provides a support and stop for the post 45. The details of the end plate 82 and the relationship of the end plate to the oval opening for a post is shown in FIG. 19.

FIG. 7 shows the top view of the H-base stand which illustrates that the stance of the stand is comparable to the stance of the step-through configuration (See FIG. 4) and thus both configurations would have substantially equivalent resistance to tipping.

FIG. 9 shows the detail of an end knob 48 received in an opening 80. This detail also applies to the relationship between the posts 20 and 22 and the openings in the elongated members 28 and 30. A t-shaped key 50 fits within the t-shaped slot 52. In this case the slot is in the end knob 48 but the same configuration is utilized to mate the posts 20 and 22 in FIG. 15. The combination of the oval shape of the post and the oval shape of the opening with the mating of the t-shaped key with the t-shaped slot creates a very rigid interconnection even before fasteners are used to secure the post to the end plates 82. The post 45 (see FIG. 5) is received in the oval opening 44 and is secured in a comparable way in the central opening 44 (see FIG. 8). The opening 44 may desirably incorporate two t-shaped keys (not shown but the same in shape and function as the key 50. The use of the t-shaped key improves the rigidity of the connection still further as may be especially desirable in a single post configuration. FIG. 9 also illustrates the incorporation in the spanner 46 of shoulders of which shoulder 81 is representative. The shoulders cooperates with the exterior surface of the support member 28 to further stabilized the joint and to provide a smooth transition from support member to spanner.

Figure 10:
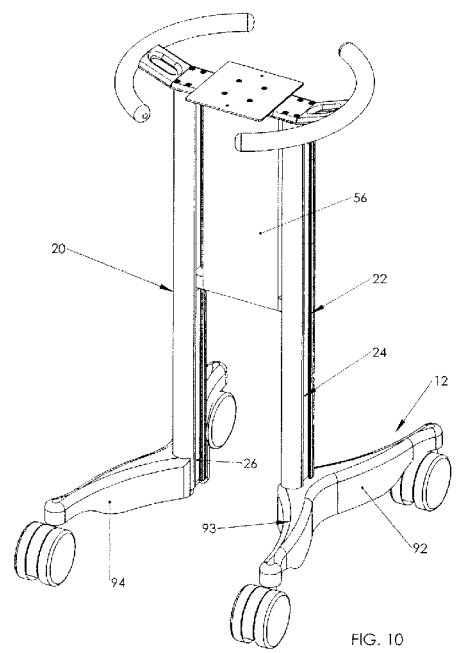
FIG. 10 is an isometric view of the step through configuration of the stand with the addition of an inter-connecting panel positioned between the support posts.
Figure 14:
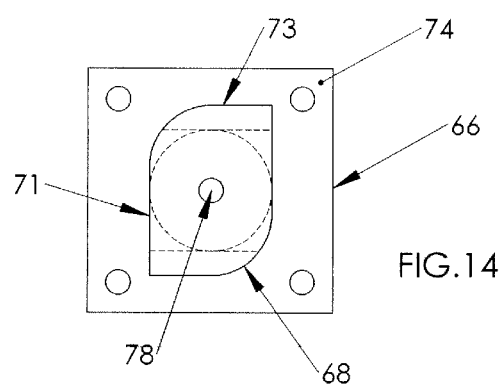
FIG. 14 is a front view of the dovetail bracket of FIG. 13.
Figure 15:
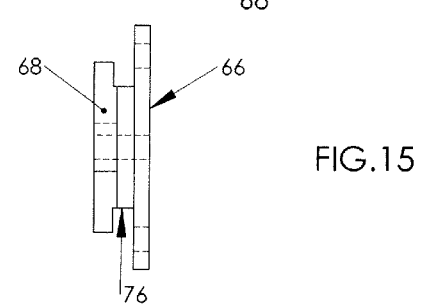
FIG. 15 is a top plan view of the dovetail bracket of FIG. 13.
Figure 13:
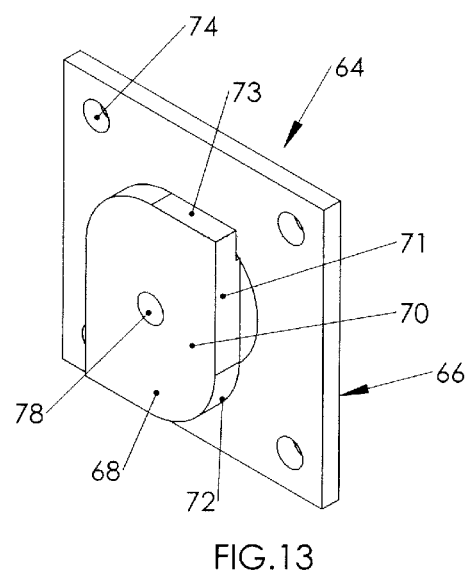
FIG. 13 is an isometric view a dovetail bracket showing the rotatable engagement flange.
Figure 16:
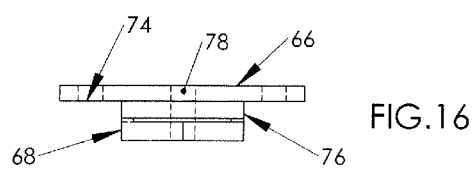
FIG. 16 is a side elevation view of the bracket of FIG. 13 showing the knob which is used to rotate the engagement flange and to pull it into tight engagement with the t-shaped slot.

Referring to FIG. 10 a step-through stand is illustrated with an optional inter-connecting panel 56. The panel spans between the posts 20 and 22 and is connected to the opposed t-shaped slots in the posts (slot 26 is visible in this view). The panel uses the availability of the t-shaped slots to provide an efficient structure for attachment through t-shaped keys (See FIGS. 23 through 26) and, once attached, the panel improves the rigidity of the configuration by limiting any flexing of the posts especially at their lower ends. Thus the structural integrity of the base 12 is improved. The flat surfaces of the panel also provide a substantial area for mounting medical devices and accessories and provides a surface on which textual and graphic material may be imprinted. The textual material may provide safety information on the use of the stand or of the supported equipment, or may display the logo of the equipment manufacturer. The preferred material for the panel is extruded aluminum.

FIG. 10 also shows the vertical sides 92 and 94 of the elongated support members 28 and 30. The sides are connected to a top portion 93 through rounded transitions from the sides.

Figure 11:
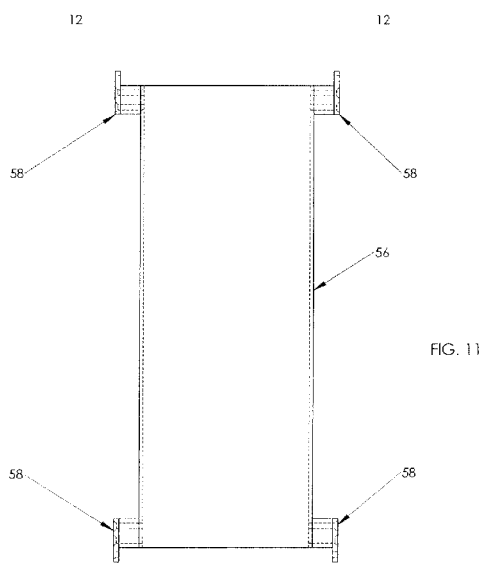
FIG. 11 is a side view of the interconnecting panel showing the positioning of dovetail brackets which are used to connect the panel to the t-shaped slots on the opposed support posts. The dovetail bracket detail is shown in FIGS. 13-16.

FIG. 11 shows the panel 56 with four t-slot keys 58 mounted near the four corners of the panel.

FIG. 12 is a sectional view of the panel taken on line 12-12 of FIG. 11 and showing the t-slot keys near the top of the panel and showing that the panel has a hollow interior 63. The t-slot keys on the exterior of the panel (flange 108 is representative) have a shape corresponding to the shape of the t-shaped slot in the posts and an engagement bolt (not shown) which may terminate in a knurled knob or a bolt head that can be rotated with a wrench to draw the key into engagement with the sides of the t-shaped slots and then tightened further to frictionally engage the walls of the slot to hold the panel firmly in position.

FIGS. 13-16 shows the structure of the dovetail bracket. The bracket illustrated is typical of all of the brackets that may be utilized in a particular installation including the brackets used to attach a piece of medical equipment to the exterior slot on a post. The bracket 64 comprises a mounting base 66 which includes mounting openings of which opening 74 is representative. A flange 70 is carried on the mounting base through a spacer 76. A threaded bore 78 passes through the base, spacer and flange 70 so that a set screw (not shown) can draw the flange into engagement with a t-shaped slot. The screw may optionally be a tamper proof set screw which requires a hex key so the that screw is not easily removed using common tools. As a further option a knob can be used as the head of the screw so that the screw can be tightened by hand where security of the attached equipment is not an issue.

Figure 22:
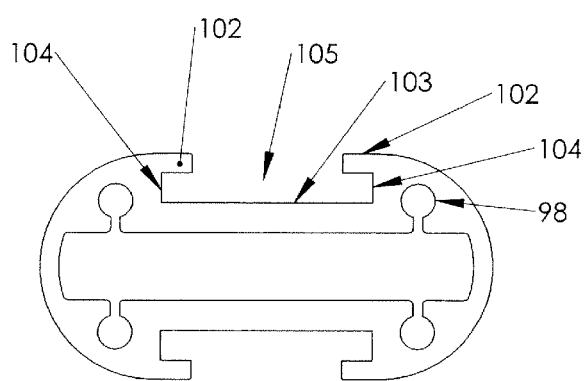
FIG. 22 is and end view of the support post.

The flange 70 is shown to have two longer flat sides 71 which are spaced a distance less than the opening defined by the walls 102 (See FIG. 22). When the flange is rotated to the position shown in FIG. 14, the flange can be inserted though the opening in a t-shaped slot (the spacer provides sufficient length so that the flange can be completely received in the slot). Then when the flange is rotated the flat sides 73 engage the inner walls 104 of the slot and prevent the removal of the flange. Further rotation of the bolt creates frictional engagement between the flange and the inner surface of wall 102, thus creating a structural interconnection between the post and any attached equipment so that the equipment (e.g. a battery pack) is securely held in position. Such a load can be mounted exteriorly as in FIG. 1, or interiorly when a panel is not utilized.

FIGS. 17-19 show the details of an elongated support member 28 with an opening 80 for receiving a post or the knob of a spanner. The walls of the opening have a series of compression ridges 88 around the curved ends of the opening. These ridges engage the end of a post or knob so that for example, a post that is slightly undersized will still be engaged in the opening and a post that is slightly over-sized can be forced into the opening by compressing the compression ridges 88.

In FIG. 19, which is an enlarged view of detail A from FIG. 18, the end plate 82 is shown to have fastener openings of which opening 90 is representative. Bolts passing through these openings enter the openings 98 of the post (see FIG. 22) and secure the posts to the floor of the openings.

As shown in FIGS. 17, 18 and 20, the elongated support member 28 has bosses 38 at either end. These bosses provide an opening for support legs or the shaft of castering wheels to be journaled. (See representative opening 95 in FIG. 18A).

FIG. 18A is a bottom view of the elongated member 28. As will appear the support member is hollow and formed by walls such as representative walls 92 and 94. These walls converge toward their outer ends and are formed to create the bosses 38 at the outer ends. This view shows the webs 96 that are molded into the space between the sides 92 and 94 to provide greater rigidity and structural integrity.

FIG. 18 is a shows the topside of an elongated support member 28. The position of the webs 96 is shown in dotted lines.

The walls 92 and 94 are higher near the center at opening 80 and taper toward the ends (See FIG. 20) to provide for the height of the engagement supports such as castering wheels. It has been determined that molded materials and specifically molded nylon or an ABS Polycarbonate blend provides the necessary strength and toughness including impact resistance to support the stand and it's associated equipment load. Xenon plastic has also been determined to be suitable.

To make the molded materials sufficient strong particularly in bending, a series of webs 96 are incorporated. These webs extend at an angle and connect between the walls 92 and 94. The exterior of the elongated support members is may receive a colored coating such as epoxy paint or powder coating. The coating is primarily for cosmetic appearance purposes and combined with the efficiency of molding of the support member provides for excellent durability.

Figure 21:
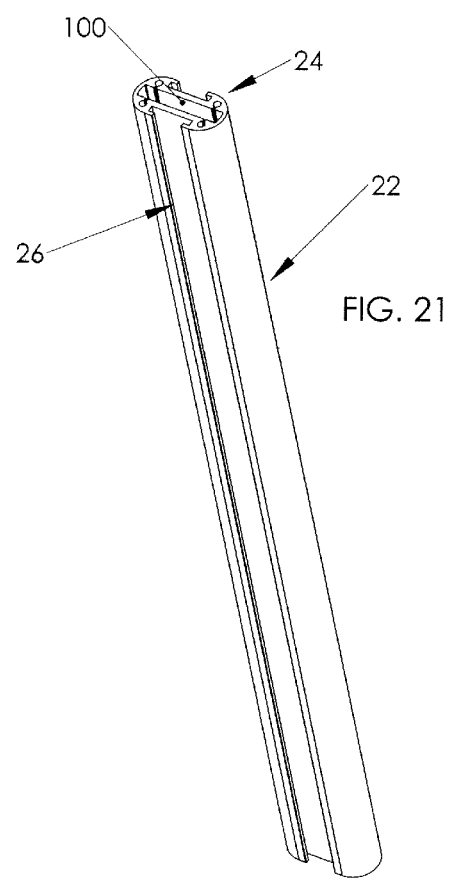
FIG. 21 is an isometric view of one of the support posts.
Figure 24:
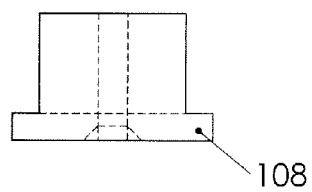
FIG. 24 is a top view of the t-shaped key.
Figure 25:
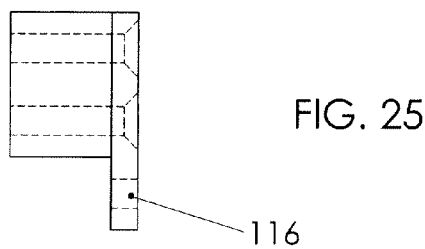
FIG. 25 is a side view of the t-shaped key.
Figure 26:
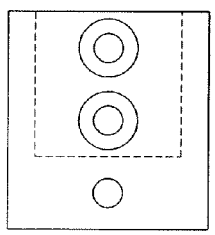
FIG. 26 is a front view of the t-shaped key.
Figure 23:
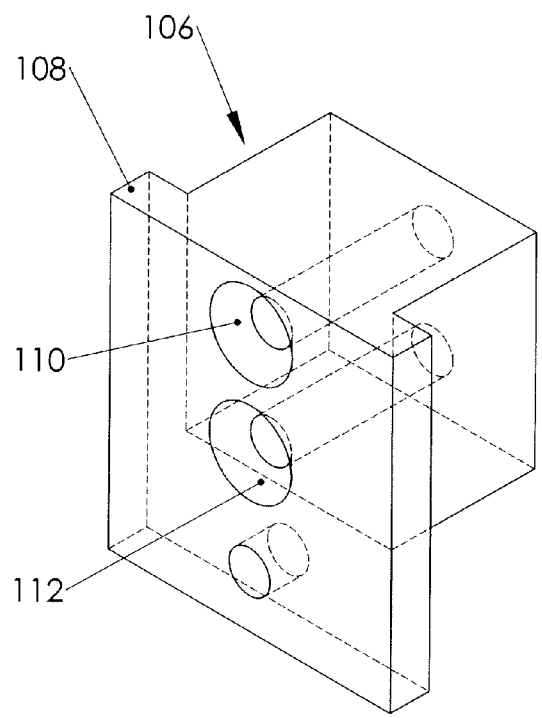
FIG. 23 is an isometric view of the T-shaped key for attaching the interconnecting panel to the support posts.

FIGS. 21 and 22 show the structural details of the posts. Post 22 is taken as representative of both posts in a two post configuration. It has a uniform cross section and so is susceptible to being extruded in a single pass. Aluminum is the preferred material. T-shaped slots 24 and 26 are formed in the exterior of the post and a central cavity 100 is formed to reduce material cost and ease the extrusion process. Referring to FIG. 22 the end detail of the post is shown. Since the extrusion is uniform the end detail reflects the structure throughout the length of the post 22. The t-shaped slot 24 is representative of both slots 24 and 26. The slot is formed between inner walls 104 which together with the rear wall 103 form an interior chamber 105. A narrowed opening is formed between walls 102. The space between the walls 102 is sufficient to pass the narrowest width of the flange of the dovetail bracket (See FIGS. 13-16, but will not pass the length of the flange of the dovetail bracket so that when the flange is rotated into contact with the walls 104 it is retained in chamber 105. The openings of which opening 98 is representative have a generally circular cross-section and may be threaded after extrusion to engage threaded bolts which pass through the end plate 82 (See FIG. 19).

FIGS. 23 to 26 show the t-shaped key 106 which is used to attach a panel 56 (see FIG. 10) between posts 22 and 20. An end plate 108 is sized to fit into the t-shaped slots in the posts. The panel is secured to the key through the openings 110 and 112. The panel is first assembled with all of the keys 106 in place. Then the flanges 108 are slid into the opposed slots on posts 22 and 20 (from the top before the cross-piece is put in place or from the bottom at any time. When the panel is at the selected vertical position a threaded fastener (not shown) is screwed into the threaded bore 116 until it engages the rear wall 103 (see FIG. 22) of a t-shaped slot and then further tightened, the flange 108 is brought into frictional engagement with the walls 102 so that it can support the load of the panel and any associated medical accessories that may be attached to the panel. Where security of the panel is an issue hex head or other unconventional fasteners can be used so that the panel can not be removed by ordinary tools.

While the medical equipment is described as being attached with dovetail brackets and the panel with t-shaped keys, it will be apparent that alternatively keys may be used with the medical equipment and dovetail brackets can be used with panels.

Various modifications and alterations of the invention will become apparent to those skilled in the art without departing from the spirit and scope of the invention, which is defined by the accompanying claims.

Any element in a claim that does not explicitly state "means for" performing a specified function or "step for" performing a specified function is not to be interpreted as a "means" or "step" clause as specified in 35 U.S.C. §112, ¶6.

What is claimed is:

1. A stand for elevated support of a load, comprising:
a support base comprising at least two elongated support members,
each of said support members having two spaced ends and a center portion adapted to mount at least four floor engagement supports,
said support base having a center of support and said center portions of said support members being spaced from said center of support on opposite sides of said center of support,
said support members being spaced to permit unimpeded access for a users feet at least substantially to said center of support, each of said support members mounting at least one post and said posts having substantial vertical extent,
said posts extending upwardly from said support base,
said posts supporting a load support platform adapted to mount one or more loads,
a spanner member extending between said support members and fixing the spacing between said support members.

2. The stand for elevated support of a load as set forth in claim 1, comprising:
said elongated support members curving toward said center of support with the central portion of said elongated support being the closest point on said elongated support to said center of support.

3. The stand for elevated support of a load as set forth in claim 1, comprising:
said elongated support members incorporating spaced walls and an interconnecting top portion.

4. The stand for elevated support of a load as set forth in claim 3, comprising:
said elongated support members having spaced walls wherein said walls are substantially vertical.

5. The stand for elevated support of a load as set forth in claim 3, comprising:
a plurality of longitudinally spaced webs bridging between said spaced walls.

6. The stand for elevated support of a load as set forth in claim 3, comprising:
said walls converging toward the ends of said elongated support member.

7. The stand for elevated support of a load as set forth in claim 6, comprising:
said support members having a vertical bore in the underside of each end to receive the vertical post of a castering wheel to serve as floor engagement supports.

8. The stand for elevated support of a load as set forth in claim 7, comprising:
the height of said elongated support members tapering from the greatest height at the central portion of said elongated support members to a lesser height at the ends and retaining sufficient height to accommodate said vertical bore.

9. The stand for elevated support of a load as set forth in claim 3, comprising:
said elongated support members adapted to mount support legs adjacent the ends of said elongated support members.

10. The stand for elevated support of a load as set forth in claim 1, comprising:
said one or more vertical posts having spaced side walls and tops walls enclosing a hollow interior.

11. The stand for elevated support of a load as set forth in claim 10, comprising:
said vertical posts having a uniform cross-section throughout said posts length.

12. The stand for elevated support of a load as set forth in claim 11, comprising:
said load platform comprising a cross piece bridging between and attached to said posts said interior of said posts having a plurality of openings at least near one of the ends thereof for receiving fasteners to attach said posts to said elongated members and said load support platform.

13. The stand for elevated support of a load as set forth in claim 10, comprising:
said side walls having t-shaped slots along the length of said posts,
said t-shaped slots having and exterior opening and an interior chamber formed by spaced walls,
a dovetail bracket having a flange with a width sized to pass through said exterior opening and a length greater than said the distance between the walls at the ends of said chamber so that the flange engages the walls at the ends of said chamber when said bracket is rotated.

14. The stand for elevated support of a load as set forth in claim 13, comprising:
said dovetail bracket having a frictional engagement knob threaded into said flanges and so that rotation of said knob first causes said flange to rotate into engagement with said walls at the end of said chamber and upon further rotation causes said flanges to frictionally engage the exterior widthwise wall of said chamber.

15. The stand for elevated support of a load as set forth in claim 1, comprising:
said elongated support members are adapted to receive said posts in an opening in the upper surface of said support members sized to receive and engage said posts.

16. The stand for elevated support of a load as set forth in claim 15, comprising:
said opening in said support members incorporates a t-shaped key for being received in a t-shaped slot of said post.

17. The stand for elevated support of a load as set forth in claim 15, comprising:
said opening has a floor member sized to bridge over the underside of said opening,
said floor member having at least one fastener bore,
said floor member supporting said post and being attached to said post by fasteners through said each least one bore.

18. The stand for elevated support of a load as set forth in claim 1, comprising:
at least one cross piece bridging between and attached to said posts.

19. The stand for elevated support of a load as set forth in claim 1, wherein:
said posts terminate at said load support platform,
said load support platform comprises a cross piece extending between and beyond said posts and supporting hand grips at the outer ends of said cross-piece.

20. The stand for elevated support of a load as set forth in claim 19, wherein:
said hand grips comprise at least part circular bars at least partially surrounding the area above said posts.

21. The stand for elevated support of a load as set forth in claim 19, wherein:
said cross-piece carrying a support plate at the central portion thereof,
said support plate adapted for carrying a load.

22. The stand for elevated support of a load as set forth in claim 21, wherein:
said support plate having fastener bores for receiving fasteners to attach said load to said plate.

23. The stand for elevated support of a load as set forth in claim 1, wherein:
said elongated support members are comprised of plastic selected from the group of:
An ABS blend, and
Nylon.

24. A stand for elevated support of a load, comprising:
a support base comprising at least two elongated support members,
each of said support members having spaced ends for mounting floor engagement supports and each having a central opening, said support base having a center of support,
said support members being spaced to permit unimpeded access for a users feet at least substantially to said center of support,
said stand having openings in said elongated support members,
said stand further including a spanner bridging between spaced elongated support members and for being secured to said support members and having engagement knobs on the ends of said spanner shaped to be received in said openings in said elongated support members,
said spanner having at least a central opening sized to receive and engage, a support post having substantial vertical extent.

25. A stand for elevated support of a load, comprising:
a support base comprising at least two elongated support members,
each of said support members having spaced ends for mounting floor engagement supports and having a central opening,
said support base having a center of support,
said support members being spaced to permit unimpeded access for a users feet at least substantially to said center of support,
said stand having oval openings in said elongated support members at least two of said support members adapted to receive support posts with an oval exterior shape,
at least two of said support posts for extending vertically from said support base when mounted in said openings in said elongated support members,
said support posts supporting a load support platform adapted to mount one or more loads,
said stand further including an optional spanner for bridging between spaced elongated support members and having end knobs conforming in their exterior configuration to said support posts and adapted to be received and secured in said openings,
said spanner having a central opening conforming to the exterior of said support posts for supporting a single central support post,
said support posts supporting a load support platform adapted to mount one or more loads.

26. A kit for a modular stand for elevated support of a load, comprising:
a support base comprising at least two elongated support members,
each of said elongated support members having spaced ends for mounting at least two floor engaging members and a central post mount opening,
said support base having a center of support,
said support members being spaced to permit unimpeded access for a users feet at least substantially to said center of support,
at least one support post adapted to extend vertically from said post mount in said support base,
said kit further including a spanner for bridging between spaced elongated support members and having end knobs conforming in their configuration to said support post and adapted to be received secured to said post mount,
said spanner having at least a central opening sized to receive and engage one of said support posts.
said one or more vertical posts adapted to support a load support platform adapted to mount one or more loads.

27. A stand for elevated support of a load, comprising:
a support base comprising at least two elongated support members,
each of said support members having spaced ends adapted to mount floor engagement supports and a having a central opening,
said support base having a center of support a center portion of said support members being spaced from said center of support on opposite sides of said center of support,
a spanner having ends adapted to be received in said openings in said elongated members to space said elongated support members a sufficient distance to permit unimpeded access for a users feet at least substantially to said center of support,
said spanner having a central opening configured to receive an oval shaped post having substantial vertical extent,
said post adapted for supporting a load at its upper end.

28. A stand for elevated support of a load, comprising:
a support base comprising at least two elongated support members,
each of said support members having spaced ends adapted to mount floor engagement supports and a having an oval central opening,
at least two oval shaped posts received in said central openings and having substantial vertical extent,
said support base having a center of support, said central openings of said support members being spaced from said center of support on opposite sides of said center of support,
a cross piece extending between said posts and fixing the distance between said posts and said elongated members at a distance determined by the length of said cross piece,
said posts adapted to support a load at their upper ends.

29. The stand of claim 28, comprising:
said openings in support members having the same shape as the exterior configuration of said posts.

* * * * *